United States Patent [19]

Pesa et al.

[11] Patent Number: 4,478,955

[45] Date of Patent: Oct. 23, 1984

[54] UPGRADING SYNTHESIS GAS

[75] Inventors: Frederick A. Pesa, Aurora; Anne M. Graham, Northfield, both of Ohio

[73] Assignee: The Standard Oil Company, Cleveland, Ohio

[21] Appl. No.: 552,556

[22] Filed: Nov. 16, 1983

Related U.S. Application Data

[63] Continuation of Ser. No. 332,772, Dec. 21, 1981, abandoned.

[51] Int. Cl.³ .................. C07C 1/04; C07C 27/06
[52] U.S. Cl. ......................... 518/713; 518/726; 502/300; 502/304; 502/305; 502/306; 502/307; 502/318
[58] Field of Search ................. 518/713, 726

[56] References Cited

U.S. PATENT DOCUMENTS

| | | |
|---|---|---|
| 2,476,788 | 7/1949 | White . |
| 2,535,060 | 12/1950 | Gresham . |
| 2,549,470 | 4/1951 | Howk et al. . |
| 4,014,913 | 3/1977 | Ellgen et al. . |
| 4,086,262 | 4/1978 | Chang et al. . |
| 4,096,164 | 6/1978 | Ellgen et al. . |
| 4,122,110 | 10/1978 | Sugier . |
| 4,162,262 | 7/1979 | Ellgen et al. . |
| 4,171,320 | 10/1979 | Vannice et al. . |
| 4,199,522 | 4/1980 | Murcheson et al. . |
| 4,206,134 | 6/1980 | Kugler . |
| 4,210,597 | 7/1980 | Huang . |
| 4,224,236 | 9/1980 | Wunder . |
| 4,235,798 | 11/1980 | Bartly . |
| 4,235,801 | 11/1980 | Bhasin . |
| 4,246,186 | 1/1981 | Bhasin et al. . |

FOREIGN PATENT DOCUMENTS

| | | |
|---|---|---|
| 4653 | 10/1979 | European Pat. Off. . |
| 4656 | 10/1979 | European Pat. Off. . |
| 5492 | 11/1979 | European Pat. Off. . |
| 18763 | 11/1980 | European Pat. Off. . |
| 715465 | 9/1954 | United Kingdom . |

OTHER PUBLICATIONS

Galvagno, J. of Cat. 69 283-291 (1981).

Primary Examiner—Howard T. Mars
Attorney, Agent, or Firm—Joseph G. Curatolo; Larry W. Evans

[57] ABSTRACT

A process is provided for the upgrading of synthesis gas to hydrocarbons and oxygenated hydrocarbons, particularly olefins and carboxylic acids by contacting synthesis gas with catalysts comprising the mixed oxides of ruthenium, copper, an alkali or alkaline earth metal, and optionally a metal selected from Ce, Cr, Fe, Mn, Mo, Th, Zn or mixtures thereof. The synthesis gas upgrading product may be contacted with a hydrogenation catalyst to provide alkanes, alcohols and esters, useful for fuels.

44 Claims, No Drawings

UPGRADING SYNTHESIS GAS

This is a continuation of application Ser. No. 332,772 filed Dec. 21, 1981 now abandoned.

TECHNICAL FIELD

The present invention is directed to the upgrading of synthesis gas to produce mixtures of hydrocarbons.

More particularly, the present invention is directed to a vapor phase reaction of synthesis gas comprising carbon monoxide and hydrogen in the presence of a catalyst to produce mixtures of hydrocarbon and oxygenated hydrocarbons, wherein olefin and carboxylic acid products predominate.

BACKGROUND OF THE INVENTION

U.S. Pat. No. 2,476,788 to White discloses the synthesis of hydrocarbons, including oxygenates such as aldehydes, ketones and alcohols from carbon monoxide and hydrogen in the presence of metals or metal oxides selected from nickel, iron or cobalt, optionally with promoter metals or metal compounds of aluminum, cerium, magnesium, manganese, thorium, titanium, uranium, zinc, and zirconium. The catalyst could be supported on suitable carriers such as clay, silica gel, and alumina.

U.S. Pat. Nos. 2,535,060 to Gresham and 2,549,470 to Howk et al. disclose the preparation of straight-chain primary hydroxyalkanes by introducing hydrogen, carbon monoxide and a hydroxylated solvent into a reaction vessel and heating the mixture in the presence of a ruthenium-containing catalyst (particularly ruthenium metal, oxide, carbonyl, or salts of carboxylic acids which give rise to formation of the carbonyl) and in Howk et al., in the presence of an alkaline reagent by maintaining pH in the range of 7.0 to 11.5. Both Gresham and Howk et al. teach that it is essential that the reaction take place in the liquid phase.

U.S. Pat. No. 4,014,913 to Ellgen et al. discloses the preparation of acetic acid, ethanol and acetaldehyde by contacting $H_2$ and CO with a rhodium-manganese catalyst.

U.S. Pat. No. 4,086,262 to Chang et al. describes the production of hydrocarbon mixtures by contacting a mixture of carbon monoxide and hydrogen with a carbon monoxide reduction catalyst and an acidic crystalline alumino silicate (zeolite). Chang et al. teach that prominent types of catalysts include metals or oxides of Zn, Fe, Co, Ni, Ru, Th, Rh, and Os, and that "with the exception of ruthenium, all practical art recognized synthesis catalysts contain chemical and structural promotors".

U.S. Pat. No. 4,096,164 discloses the production of oxygenated 2 carbon atom hydrocarbons by reacting CO and $H_2$ in the presence of catalysts comprising Rh, Mo and W.

U.S. Pat. No. 4,122,110 to Sugier et al. discloses the manufacture of linear saturated primary alcohols from synthesis gas using a catalyst comprising copper, cobalt, a third metal selected from chromium, iron, vanadium and manganese, at least one alkali metal and optionally zinc.

U.S. Pat. No. 4,162,262 to Ellgen et al. discloses the production of 2 carbon atom oxygenated hydrocarbons while minimizing co-production of methanol by reacting $H_2$ and CO with a catalyst containing rhodium metal, uranium or thorium and optionally iron, molybdenum or tungsten.

U.S. Pat. No. 4,171,320 to Vannice discloses the selective production of olefins from carbon monoxide and hydrogen using as a catalyst ruthenium on a support comprising at least one refractory Group VB metal oxide.

U.S. Pat. No. 4,199,522 to Murchison et al. discloses the preparation of olefins of 2 to 4 carbon atoms from carbon monoxide and hydrogen using catalysts comprising a sulfide, oxide or metal of Mo, W, Re, Ru, Ni, Pd, Rh, Os, Ir or Pt and a hydroxide, oxide or salt of Li, Na, K, Rb, Cs, Mg, Ca, Sr, Ba or Th.

U.S. Pat. No. 4,201,597 to Huang et al. discloses the preparation of oxygenated hydrocarbons by reacting carbon monoxide and hydrogen in the presence of a catalyst containing rhodium, tungsten and an alkali metal.

U.S. Pat. No. 4,206,134 to Kugler et al. discloses the selective preparation of low weight olefins from carbon monoxide and hydrogen using a a catalyst ruthenium on a support consisting of a manganese-containing oxide.

U.S. Pat. No. 4,235,801 to Bhasin discloses the preparation of ethanol by contacting a synthesis gas mixture containing CO and $H_2$ with a rhodium-iron catalyst.

U.S. Pat. No. 4,246,186 to Bhasin et al. discloses the preparation of two carbon atom oxygenated hydrocarbons from hydrogen and carbon monoxide by reaction with a rhodium metal catalyst, as compared to other single element Group VIII metal and copper catalysts.

European patent appln. No. 18,763 by Ball et al. describes the production of oxygenated hydrocarbons having 1 to 4 carbon atoms by reaction of CO and $H_2$ in the presence of a catalyst comprising rhodium, chromium and optionally Fe, Mn, Mo, W or Ru. The catalyst may be prepared upon a support which has been formerly activated by the addition of metals or nonmetals such as alkalis, Th, Mn, Rh, Fe, Cr, Mo, B, and P.

European patent appln. Nos. 4,653 and 4,656 by Hoechst A.G. describe the production of acetic acid, ethanol and acetaldehyde by reacting CO and $H_2$ with a catalyst containing rhodium, magnesium and a halide.

SUMMARY OF THE INVENTION

It is an object of the present invention to provide a process to upgrade synthesis gas to produce hydrocarbons, particularly olefins, and oxygenated hydrocarbons, particularly carboxylic acids, with high selectivity.

It is a further object of the present invention to provide novel catalyst compositions useful in the upgrading of synthesis gas to produce olefins and oxygenated hydrocarbons, particularly carboxylic acids.

We have found that catalysts comprising the mixed oxides of ruthenium, copper and an alkali metal, optionally promoted with an oxide of at least one of Ce, Cr, Fe, Mn, Mo, Th, Zn or mixtures thereof, said catalysts being optionally nitrided, are useful for the upgrading of synthesis gas to hydrocarbons, particularly olefins, and oxygenated hydrocarbon products, particularly carboxylic acids.

In general, the process of the present invention includes the upgrading of synthesis gas to obtain selectivity to olefins and carboxylic acids comprising contacting carbon monoxide and hydrogen in the vapor phase at a reaction temperature of at least 250° C. and a reaction pressure of at least 500 psi with a catalyst of the formula $$M_aA_bRuCu_cN_zO_x$$

wherein
A is an alkali metal or an alkaline earth metal or mixtures thereof,
wherein
M is Ce, Cr, Fe, Mn, Mo, Th, Zn or mixtures thereof, and
wherein
a is 0 to about 0.5
b is about 0.002 to about 2,
c is about 0.5 to about 3,
z is 0 to about 1 weight percent and
x is the number of oxygens needed to fulfill the valence requirements of the other elements.

The present invention further includes novel catalysts of the composition $$M_aA_bRuCu_cN_zO_x$$

wherein
A is an alkali metal or an alkaline earth metal or mixtures thereof,
wherein
M is Ce, Cr, Fe, Mn, Mo, Th, Zn or mixtures thereof, and
wherein
a is 0 to about 0.5
b is about 0.002 to about 2,
c is about 0.5 to about 3,
z is 0 to about 1 weight percent and
x is the number of oxygens needed to fulfill the valence requirements of the other elements.

The present invention further includes the upgrading of synthesis gas to yield hydrocarbons, namely alkanes, alcohols and esters useful for fuels, comprising:

contacting carbon monoxide and hydrogen in the vapor phase at a temperature of at least 250° C. and a pressure of at least 500 psi in the presence of a catalyst of the formula $$M_aA_bRuCu_cN_zO_x$$

wherein
A is an alkali metal or an alkaline earth metal or mixtures thereof,
wherein
M is Ce, Cr, Fe, Mn, Mo, Th, Zn or mixtures thereof, and
wherein
a is 0 to about 0.5
b is about 0.002 to about 2,
c is about 0.5 to about 3,
z is 0 to about 1 weight percent and
x is the number of oxygens needed to fulfill the valence requirements of the other elements.
recovering the hydrocarbon and oxygenated hydrocarbon products;
contacting said products with hydrogen at elevated temperature and pressure in the presence of a hydrogenation catalyst.

DETAILED DESCRIPTION OF THE INVENTION

In the process of the present invention, synthesis gas, or a mixture of carbon monoxide and hydrogen, is reacted in the presence of a carbon monoxide hydrogenation catalyst in the vapor phase to form hydrocarbons, and in particular, olefins and carboxylic acids.

Synthesis gas may be produced by means known in the art and practiced commercially, including providing synthesis gas as a product of the partial combustion of coal, natural gas, petroleum bottoms or other carbonaceous materials. One method of derivation is the heating of coke in the presence of air and then steam. The ratio of carbon monoxide to hydrogen in the synthesis gas mixture to be upgraded may vary from about 1:10 to 10:1 and is preferably in the range of about 1:3 to about 3:1. The synthesis gas may contain a very low amount of sulfur compounds, and may also contain small amounts of carbon dioxide, nitrogen and other inerts.

Although synthesis gas is a preferred reactant, any other gas composed primarily of hydrogen and carbon monoxide and having $CO:H_2$ ratio of 1:10 to 10:1 may be employed. Preferably the gaseous reactant is essentially sulfur free.

Process Conditions

The process of the present invention is carried out by contacting the gaseous reactants containing carbon monoxide and hydrogen, with the novel catalyst described below in a suitable fluid bed or fixed bed reactor. The reaction can be conducted continuously or in a batch-type operation. The reaction temperature should be maintained between about 250° C. to about 400° C., preferably 275° C. to about 375° C.

The reaction pressure should normally be maintained between about 500 psi to about 5,000 psi, preferably 500 psi to about 1500 psi. The reactant gases may be fed to the reactor utilized at a space velocity (liters gaseous reactants fed per liters of catalyst per hour) of about 100 per hour to about 10,000 per hour, preferably about 500 per hour to 6,000 per hour.

The contact time of the reactants with the catalyst is generally between about 10 seconds to about 200 seconds, and is preferably about 15 seconds to about 100 seconds.

Catalyst

The novel catalyst provided by the present invention is believed to be an oxide complex and comprises the composition described by the empirical formula $$M_aA_bRuCu_cN_zO_x$$

wherein
A is an alkali metal or an alkaline earth metal or mixtures thereof,
wherein
M is Ce, Cr, Fe, Mn, Mo, Th, Zn or mixtures thereof, and
wherein
a is 0 to about 0.5
b is about 0.002 to about 2,
c is about 0.5 to about 3,
z is 0 to about 1 weight percent and
x is the number of oxygens needed to fulfill the valence requirements of the other elements.

A may be selected from Na, Li, K, Rb, Cs, Be, Ms, Ca, Sr and Ba although Na, Li, Rb, Cs and Mg are preferred.

The ratio of ruthenium to copper is preferably about 0.5:1 to about 2:1. An oxide of alkali metal or an alkaline earth metal, preferably an alkali metal, is required in the present catalyst. Mixed oxide catalysts of ruthenium and copper which are alkali metal and alkaline earth metal free produce essentially all methane. The alkali metal or alkaline earth metal may be present in the catalyst at a level of about 0.002 to about 2 moles per mole of ruthenium oxide, most preferably about 0.02 to about 0.4. Preferred is a level of about 0.02 to about 1 mole alkali metal per mole of ruthenium oxide. The level of alkaline earth metal, if present, to ruthenium oxide is preferably 0.02 to about 0.5 moles per moles of ruthenium oxide. Preferably the M promoter is present in a level of 0.1 to 0.5 moles per mole of ruthenium oxide.

The catalyst of the present invention is a mixed metal oxide. In the process of the present invention, the catalyst is preferably utilized in a partially reduced state, however, the catalyst is not totally reduced to elemental metal and thus retains its oxide character.

The catalyst may be prepared by conventional means, such as mixing compounds containing the catalyst components in a liquid solution or slurry, such as a water solution or slurry and heating, recovering the catalyst precursor from the liquid, drying and calcining. Suitable catalyst component containing compounds may include but are not limited to oxides, hydroxides, inorganic salts such as nitrates, phosphates, halides, carbonates, silicates, aluminates, and salts of organic acids such as acetates, formates, butyrates, propionates, benzylates, and the like. Preferred catalysts of the present invention, containing the alkali metal component are prepared by recovering the catalyst precursor by adding to the aqueous solution of ruthenium, copper and promoter (if any) components, an alkali metal hydroxide to cause precipitation of the catalyst precursor, heating in the presence of the alkali metal, and thereafter filtering the precipitate.

The catalyst may be formed in a conventional manner, such as tabletting, pelleting, or supporting the active catalyst material on a carrier. The carrier is preferably inert, and may include silica, alumina, Alundum, clay, alumina-silica, silicon carbide and the like. The active catalytic material may be coated on the carrier by the method described in U.S. Pat. No. 4,077,912 or may be impregnated on the carrier such as by depositing a solution of the catalyst component containing compounds onto a carrier, drying and calcining. Catalyst components may be added to the carrier separately, if desired.

Products

Products of the synthesis gas upgrading process of the present invention include methane, gaseous alkanes having more than one carbon atom and olefins having from 2 carbon atoms to about 4 carbon atoms; alcohols, carboxylic acids and aldehydes having from one to 5 carbon atoms present in an aqueous product phase; and olefins, carboxylic acids, esters, aldehydes and alcohols in an organic or oil product phase. Generally, very low amounts of higher weight paraffins are produced. The predominant products, however, are olefins and carboxylic acids.

Products of the synthesis gas upgrading process include, among others, methane, ethane, propane, butane, ethylene, propylene, butylene, methanol, ethanol, propanol, butanol, pentanol, acetic acid, propionic acid, butyric acid, valeric acid, and low amounts of aldehydes and esters including acetaldehyde and methyl butyrate. These products are useful as chemical feedstocks, or as fuels, such as in gasoline mixtures. Where conversion is maintained at a moderate or low level, these products can be recovered from the reactor effluent, and the remaining synthesis gas recycled to the reaction.

Alkanes, esters and alcohols are most suitable for use as fuels, such as in gasoline mixtures. Therefore, in one embodiment of the invention, the liquid product mixture obtained from the synthesis gas upgrading process (containing in addition to alcohols and esters, the non-fuel components such as olefins, aldehydes and carboxylic acids) is contacted with hydrogen at elevated temperature and pressure in the presence of a hydrogenation catalyst. The resulting hydrogenation products, alkanes, alcohols and esters, are suitable for use as fuel components.

The hydrogenation process may be conducted in the vapor phase, at a reaction temperature of about 150° C. to about 450° C. and a reaction pressure of about 250 psig to about 5000 psig. Any suitable hydrogenation catalyst, such as nickel or copper chromite may be used, although catalysts such as those disclosed in U.S. Ser. No. 264,744, assigned to our common assignee, are preferred. These catalysts may be represented by the formula:

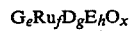

$G_e Ru_f D_g E_h O_x$ wherein
G=Zn, Cd and mixtures thereof;
D=Co, Ni and mixtures thereof;
E=Fe, Cu, Rh, Pd, Os, Ir, Pt and mixtures thereof;
and wherein
e=0 to 1,
f=0.01 to 3,
g=0.01 to 3,
h=0 to 1,
x=the number of oxygens determined by the valence requirements of the other elements.

SPECIFIC EMBODIMENTS

Catalyst Preparation

In the examples below, catalysts were prepared by the following method. An amount of ruthenium chloride and copper chloride required to give 0.03 moles of each metal were dissolved in 250 milliliters of water with stirring for 30 minutes. Aqueous sodium hydroxide (50% by weight) was added dropwise, with stirring, until the pH reached and remained at 8.3 to 8.5 (approximately 7 to 15 milliliters). The resulting slurry was heated near boiling for 30 minutes with constant stirring, then cooled. The pH was adjusted if necessary to 7.5. The mixture was filtered, washed, and reslurried with subsequent filtering and washing steps until the molar ratio of sodium to ruthenium present was approximately 0.02 to 0.2:1. The solid mixed oxide was dried at 125° C. for about 16 hours, was calcined for three hours at about 350° C. (in air) and was ground to pass 140 mesh (0.105 millimeters).

The catalysts were coated upon alumina-silica supports in the following manner. 25 grams of Norton SA 5223 Alundum, 10/30 mesh (0.595 millimeters–2.00 millimeters) were placed in a vessel. 1 25 g distilled water was sprayed onto the Alundum which was rolled for approximately 10 minutes and the procedure was repeated. The metal oxide catalysts, in an amount calculated to give a total of 0.015 moles of active metal, was added in two equal portions with 15 minutes rolling after each. The coated catalyst was dried for about 16 hours at 125° C. and calcined three hours at 350° C. Catalysts prepared in this manner contain approximately 5 weight percent active metals, 0.01% to 0.1% by weight sodium and have surface areas of about 2 $m^2/g$, with pore volumes of from about 0.06 to about 0.09 cc/g. Promoter elements were added either before precipitation of the RuCu precursor, or the RuCu oxide containing powder was impregnated with a solution of the promoter compound.

The catalysts were partially reduced in the following manner. A 20 cc stainless steel tube reactor was packed with catalyst, and hydrogen gas was introduced into the reactor at 150–200 cc/min. at atmospheric pressure. The electric block furnace placed around the reactor was increased in 50° increments stepwise until 500° C. was reached. The final temperature was maintained for two hours, at which time the reactor was allowed to cool with hydrogen flow being continued.

Certain catalysts identified below were nitrided after reduction by contacting the catalyst with ammonia for several hours at atmospheric pressure and a temperature of about 400° C., with subsequent cooling under ammonia. The nitrided catalysts contained up to 1 weight % nitrogen, as is preferred. Between 0.5 and 1 weight percent nitrogen is most preferred.

Reaction Procedure

Following catalyst reduction (and nitriding if applicable) and subsequent cooling to room temperature, the reactor was charged to the desired pressure with hydrogen. The split block electric furnace surrounding the reactor was activated and set for run temperature. The system was allowed to equilibrate for at least 15 minutes at run temperature before carbon monoxide flow was started and both gases were adjusted to the desired flow rates. After about one to one and one-half hours of reaction, the off-gas (effluent) was sampled and analyzed and the condensible product diverted from a pre-run receiver to a product collection receiver. A recovery run proceeded for one to three hours during which time the off-gas was analyzed by gas chromatography and its volume measured. The liquid product also was weighed and analyzed.

In addition to gas chromatography analysis for the gas phase, hydrocarbons having more than three carbon atoms were determined by flame ionization detection. Liquid phase hydrocarbons and oxygenated hydrocarbons were analyzed by gas chromatography. The results reported in the Tables below were calculated as follows.

Selectivity =

$$\frac{\text{Moles Product} \times \text{number of carbon atoms in product}}{\text{Moles CO input} - \text{Moles CO effluent}} \times 100$$

CO Conversion =

$$\frac{\text{Moles of CO input} - \text{moles CO effluent} \times 100}{\text{Moles of CO input}}$$

Selectivity to gas and aqueous phase products are reported as a percent of total products. Selectivity to oil phase products are reported as a percent of total oil phase product obtained, calculated as above. Weight percent hydrocarbons are reported as weight percent of total product weight. Carbon dioxide and water are not considered in the calculations.

The catalysts identified in the examples below were prepared according to the catalyst preparation methods set forth above. The catalysts were reduced, and where identified were nitrided, and tested for synthesis gas upgrading by the reaction procedure set forth above. Reaction conditions and test results are set forth in the Tables below.

EXAMPLES 1-2

Catalysts of the formula 5% $Na_bRuCuO_x$/95% Alundum were prepared according to the procedure first set forth above. Products of the synthesis gas upgrading reaction utilizing these catalysts were predominantly olefins and carboxylic acids.

EXAMPLES 3-4

Catalysts of formula 5% $Na_bRuCu_2O_x$/95% Alundum were prepared according to the procedure of Example 1 except that twice the level of copper chloride was utilized in the catalyst preparation. Product selectivity to olefins and paraffins increased, with good selectivity to carboxylic acids remaining.

EXAMPLE 5

The catalyst 5% $Na_bRuCuN_zO_x$/95% Alundum was prepared by nitriding the catalyst of Example 1 by the nitriding procedure set forth above. The catalyst continued to show selectivity to olefins and carboxylic acids, with an increase in alcohol production.

EXAMPLE 6

A catalyst of the formula 5% $Na_bRuCuO_x$/95% Alundum was prepared according to the procedure of Example 1. The predominant products of synthesis gas upgrading using this catalyst were carboxylic acids and olefins.

EXAMPLES 7-14

Catalysts of the formula 5% $Na_bRuCuN_zO_x$/95% Alundum were prepared according to the procedure of Example 5. Predominant products again were olefins and carboxylic acids.

EXAMPLES 15-23

The promoter metals listed below were added by coprecipitation or in the initial catalyst component slurry, or were added by impregnating the $RuCuO_x$ containing powder to form 5% $M_aNa_{0.02-0.2}RuCuN_zO_x$/95% Alundum catalysts by the method first set forth above, with nitriding. The catalysts were tested for synthesis gas upgrading under the conditions listed in Table III. These catalysts also exhibit good selectivity to olefins and carboxylic acids.

| Example No. | Promoter ($M_a$) | Compound | Addition |
|---|---|---|---|
| 15 | $Ce_{0.2}$ | cerium oxide | initial slurry |
| 16 | $Cr_{0.2}$ | chromium chloride | coprecipitation |
| 17 | $Fe_{0.1}$ | iron chloride | coprecipitation |
| 18 | $Mn_{0.2}$ | manganese chloride | coprecipitation |
| 19 | $Mn_{0.2}$ | manganese chloride | coprecipitation |
| 20 | $Mo_{0.1}$ | ammonium heptamolybdate | coprecipitation |
| 21 | $Mo_{0.1}$ | ammonium heptamolybdate | coprecipitation |
| 22 | $Th_{0.2}$ | thorium nitrate | impregnation |
| 23 | $Zn_{0.5}$ | zinc nitrate | impregnation |

COMPARATIVE EXAMPLES 24-25

Alkali metal/alkaline earth metal-free catalysts of the formula 5% $RuCuN_zO_x$/95% Alundum were prepared from a solution of ruthenium nitrate and copper nitrate, with nitriding of the catalyst being conducted after partial reduction. The catalysts were tested for synthesis gas upgrading under the conditions listed in Table IV, resulting in predominantly methane production.

EXAMPLES 26-35

The alkali and alkaline earth metals listed below were added to form the catalysts listed in Table IV by impregnation of either $RuCuO_x$ or $RuCuNa_{0.3}O_x$ catalysts, prepared with nitriding. These catalysts exhibit good selectivity to olefins and carboxylic acids as reported in Table IV.

| Example No. | $A_b$ Promoter Added | Compound Added | Base Catalyst |
|---|---|---|---|
| 26 | $Na_{0.2}$ | sodium carbonate | $RuCuNa_{0.3}O_x$ |
| 27 | $Li_{0.2}$ | lithium hydroxide | $RuCuNa_{0.3}O_x$ |
| 28 | $Li_{0.2}$ | lithium hydroxide | $RuCuNa_{0.3}O_x$ |
| 29 | $Mg_{0.2}$ | magnesium hydroxide | $RuCuNa_{0.3}O_x$ |
| 30 | $Mg_{0.2}$ | magnesium hydroxide | $RuCuNa_{0.3}O_x$ |
| 31 | $Na_{0.2}$ | sodium carbonate | $RuCuO_x$ |
| 32 | $Na_{0.2}$ | sodium carbonate | $RuCuNa_{0.3}O_x$ |
| 33 | $Cs_{0.2}$ | cesium acetate | $RuCuO_x$ |
| 34 | $Li_{0.4}$ | lithium hydroxide | $RuCuO_x$ |
| 35 | $Li_{0.4}$ | lithium hydroxide | $RuCuO_x$ |

EXAMPLE 36

A catalyst of the formula 5% $Na_{0.02-0.2}RuCuN_zO_x$/95% $SiO_2$ was prepared according to the method of Example 5 except that silica was substituted for the alumina silica-Alundum support. The catalyst was tested for synthesis gas upgrading at a temperature of 350° C., a pressure of 1300 psi, a space velocity of 3300 per hour and a $CO:H_2$ ratio of 3:7. CO conversion was 31.2% and the product distribution was as follows.

| Product | Wt. % |
|---|---|
| Alkanes | 28.9 |
| Olefins | 30.5 |
| Carboxylic Acid | 20.3 |
| Alcohols | 13.0 |
| Aldehydes | 1.8 |
| Esters | 5.4 |

This catalyst exhibited good selectivity to olefins and carboxylic acids.

As an example of the product mixture produced by the inventive process, the products obtained by testing the catalyst of Example 34 are as follows.

| Product | Wt. (g) |
|---|---|
| Methane | 0.2832 |
| Ethane | 0.0500 |
| Propane | 0.1393 |
| Ethylene | 0.0681 |
| Propylene | 0.2850 |
| Methanol | 0.0278 |
| Ethanol | 0.0291 |
| Propanol | 0.0093 |
| Butanol | 0.0111 |
| Pentanol | 0.0043 |
| Acetic Acid | 0.0585 |
| Propionic Acid | 0.0369 |
| Butyric Acid | 0.0202 |
| Valeric Acid | 0.0097 |
| Higher Alkanes | 0.0528 |
| Higher Olefins | 0.2097 |
| Higher Alcohols | 0.1656 |
| Higher Acids | 0.3635 |
| Aldehydes | 0.0501 |
| Esters | 0.0383 |

EXAMPLE 37

A portion of the liquid products of the process of the present invention, comprising mainly carboxylic acids and olefins, with minor amounts of alcohols and aldehydes, was hydrogenated in the vapor phase at a reaction temperature of 200° C. and a pressure of 1000 psi in the presence of a hydrogenation catalyst comprising 5% $RuCoPdZn_{0.4}O_x$ on 95% Alundum. Hydrogen was introduced to the reaction at 300 cc/minute, and hydrocarbon liquid was introduced to the reaction at 5 cc/hr. Olefins and aldehydes were completely converted to alkanes and alcohols, and over 90% of the acids were converted to either alcohols or esters. The hydrogenated products of the process of the present invention, alkanes, alcohols and esters, are useful for fuels.

Thus it should be apparent to those skilled in the art that the subject invention accomplishes the objects set forth above. It is to be understood that the subject invention is not to be limited by the examples set forth herein. These have been provided merely to demonstrate operability and the selection of catalyst component containing compounds, catalyst formulations, synthesis gas component ratios and reaction conditions can be determined from the total specification disclosure provided without departing from the spirit of the invention herein disclosed and described, the scope of the invention including equivalent embodiments, modifications and variations that fall within the scope of the attached claims.

TABLE I

Synthesis Gas Upgrading Using Promoted 5% $RuCuO_x$/95% Alundum Catalysts

| Ex. No. | Catalyst | Temp. °C. | Pressure (psi) | Space Vel. $(hr^{-1})$ | $CO:H_2$ Ratio | % CO Conversion | Product Phase, Wt. % (a) | | |
|---|---|---|---|---|---|---|---|---|---|
| | | | | | | | Gas | Aqueous | Organic |
| 1 | $Na_bRuCuO_x$ | 350 | 1300 | 3300 | 3:7 | 42.2 | 45.5 | 17.8 | 36.7 |
| 2 | $Na_bRuCuO_x$ | 350 | 600 | 510 | 1:1 | 71.4 | 18.7 | 12.9 | 68.4 |
| 3 | $Na_bRuCu_2O_x$ | 350 | 1300 | 3300 | 3:7 | 79.4 | 41.8 | 9.6 | 48.7 |
| 4 | $Na_bRuCu_2O_x$ | 350 | 600 | 510 | 1:1 | 98.1 | 30.1 | 2.3 | 67.5 |
| 5 | $Na_bRuCuN_zO_x$ | 350 | 1300 | 3300 | 3:7 | 31.2 | 56.4 | 12.5 | 31.1 |
| 6 | $Na_bRuCuO_x$ | 350 | 1300 | 3300 | 3:7 | 35.6 | 34.2 | 14.8 | 51.0 |
| 7 | $Na_bRuCuN_zO_x$ | 350 | 1300 | 3300 | 3:7 | 34.9 | 38.0 | 19.9 | 42.1 |
| 8 | $Na_bRuCuN_zO_x$ | 350 | 1300 | 3300 | 3:7 | 32.4 | 33.4 | 16.5 | 50.1 |
| 9 | $Na_bRuCuN_zO_x$ | 350 | 1300 | 3300 | 3:7 | 59.1 | 43.7 | 9.5 | 46.8 |
| 10 | $Na_bRuCuN_zO_x$ | 340 | 1300 | 3300 | 3:7 | 35.4 | 25.7 | 13.3 | 61.0 |
| 11 | $Na_bRuCuN_zO_x$ | 340 | 1300 | 3300 | 3:7 | 35.6 | 33.8 | 14.2 | 52.0 |
| 12 | $Na_bRuCuN_zO_x$ | 340 | 1300 | 3300 | 3:7 | 31.8 | 24.3 | 12.9 | 62.7 |

TABLE I-continued

Synthesis Gas Upgrading Using Promoted 5% $RuCuO_x$/95% Alundum Catalysts

| Ex. No. | Catalyst | Temp. °C. | Pressure (psi) | Space Vel. $(hr^{-1})$ | $CO:H_2$ Ratio | % CO Conversion | Product Phase, Wt. % (a) Gas | Aqueous | Organic |
|---|---|---|---|---|---|---|---|---|---|
| 13 | $Na_bRuCuN_zO_x$ | 320 | 1000 | 5500 | 3:7 | 4.0 | 18.9 | 24.3 | 56.8 |
| 14 | $Na_bRuCuN_zO_x$ | 345 | 1300 | 3300 | 3:7 | 39.4 | 48.2 | 9.9 | 41.9 |

(a) excludes weight of $H_2O$ and $CO_2$
b = 0.02 to 0.2
z = 0.5–1 wt. % active catalyst

TABLE II

Synthesis Gas Upgrading

| Ex. No. | % Selectivity (Total) Gas Phase | | | % Selectivity (Total) Aqueous Phase | | % Selectivity Organic Phase | | | | | Wt. % Paraffin |
|---|---|---|---|---|---|---|---|---|---|---|---|
| | Alkanes $CH_4$ | $\geq C_2$ | Olefins | Alcohol | Carboxylic Acid | Alcohol | Carboxylic Acid | Ester | Aldehyde | Olefin | |
| 1 | 9.9 | 5.4 | 16.4 | 1.3 | 5.6 | 17.1 | 42.2 | — | 15.6 | 25.0 | tr |
| 2 | 1.8 | 0.8 | 3.3 | 0.4 | 1.8 | 20.1 | 48.5 | — | 5.3 | 26.1 | — |
| 3 | 10.4 | 5.3 | 13.6 | 1.4 | 2.4 | 18.4 | 28.7 | 3.0 | 3.2 | 46.7 | 33 |
| 4 | 4.3 | 4.2 | 14.4 | 0.6 | 0.3 | 20.1 | 25.0 | 9.6 | 2.1 | 43.2 | 28 |
| 5 | 12.0 | 8.3 | 32.3 | 1.9 | 4.8 | 33.7 | 39.4 | 1.1 | 9.7 | 16.2 | tr |
| 6 | 7.3 | 5.6 | 15.4 | 1.3 | 4.2 | 16.7 | 43.7 | 2.8 | 8.5 | 28.3 | 4 |
| 7 | 4.4 | 5.9 | 9.9 | 1.0 | 3.6 | 15.9 | 52.5 | 1.3 | 3.6 | 26.7 | 5 |
| 8 | 7.7 | 6.4 | 11.9 | 1.3 | 3.9 | 15.3 | 44.1 | 2.5 | 7.4 | 30.8 | — |
| 9 | 11.1 | 6.4 | 13.3 | 1.3 | 2.8 | 17.9 | 35.2 | 2.3 | 7.1 | 37.5 | 5 |
| 10 | 3.6 | 5.6 | 9.3 | 1.1 | 4.2 | 16.5 | 43.4 | 2.6 | 11.2 | 26.3 | 2 |
| 11 | 7.2 | 4.4 | 8.2 | 0.9 | 3.7 | 13.1 | 44.1 | 2.1 | 12.0 | 28.8 | 2 |
| 12 | 4.8 | 5.2 | 10.3 | 0.5 | 4.6 | 13.4 | 40.0 | 2.1 | 11.6 | 32.9 | 2 |
| 13 | 8.2 | — | 3.2 | 0.5 | 7.5 | 7.7 | 69.3 | 4.0 | 10.8 | 8.2 | — |
| 14 | 3.7 | 9.0 | 28.2 | 0.9 | 3.3 | 12.8 | 49.2 | 3.0 | 4.7 | 30.4 | 2 |

*Trace aldehydes present

TABLE III

Synthesis Gas Upgrading Using 5% $M_aNa_bCuRuN_zO_x$/95% Alundum Catalysts

| Ex. No. | $M_a$ Promoter | Temp. (°C.) | Pressure (psig) | Space Velocity $(hr^{-1})$ | % CO Conv. | Weight % Useful Products | | | | | |
|---|---|---|---|---|---|---|---|---|---|---|---|
| | | | | | | Alkanes | Olefins | Carboxylic Acids | Alcohols | Aldehydes | Esters |
| 15 | $Ce_{0.2}$ | 340 | 1300 | 3300 | 92.4 | 51.2 | 24.2 | 13.3 | 9.4 | 0.4 | 1.5 |
| 16 | $Cr_{0.2}$ | 350 | 1300 | 3300 | 82.9 | 51.5 | 24.7 | 14.9 | 7.6 | 0.4 | 0.9 |
| 17 | $Fe_{0.1}$ | 300 | 1000 | 5500 | 9.5 | 45.0 | 14.9 | 18.5 | 9.6 | 3.9 | 1.3 |
| 18 | $Mn_{0.2}$ | 310 | 1000 | 5500 | 10.9 | 30.9 | 28.9 | 24.1 | 6.8 | 7.2 | 2.0 |
| 19 | $Mn_{0.2}$ | 315 | 1300 | 3300 | 60.4 | 41.1 | 29.7 | 16.7 | 7.0 | 2.9 | 2.5 |
| 20 | $Mo_{0.1}$ | 320 | 1000 | 5500 | 15.1 | 61.4 | 23.2 | 9.0 | 8.3 | — | — |
| 21 | $Mo_{0.1}$ | 350 | 1000 | 5500 | 40.6 | 47.4 | 22.8 | 15.1 | 13.8 | 0.8 | — |
| 22 | $Tb_{0.2}$ | 340 | 1300 | 3300 | 38.3 | 29.1 | 34.0 | 21.8 | 10.1 | 2.9 | 2.2 |
| 23 | $Zn_{0.5}$ | 340 | 1300 | 3300 | 4.4 | 48.7 | 34.7 | 4.3 | 12.3 | — | — | b = 0.02–0.2
z = 0.5–1 wt. % active catalyst
$CO:H_2$ ratio = 3:7

TABLE IV

Synthesis Gas Upgrading Using 5% $A_bRuCuN_zO_x$/95% Alundum Catalysts

| Ex. No. | $A_b$ Promoter | Temp. (°C.) | Pressure (psig) | Space Velocity $(hr^{-1})$ | % CO Conversion | Weight % Useful Products | | | | | |
|---|---|---|---|---|---|---|---|---|---|---|---|
| | | | | | | Alkanes | Olefins | Carboxylic Acids | Alcohols | Aldehydes | Esters |
| C 24 | — | 360 | 1300 | 3300 | tr | 100 | — | — | — | — | — |
| C 25 | — | 320 | 1000 | 5500 | tr | 70.9 | — | 15 | 14.1 | — | — |
| 26 | $Na_{0.5}$ | 320 | 1000 | 5500 | 6.6 | 12.5 | 15.8 | 49.2 | 11.4 | 7.6 | 3.5 |
| 27 | $Li_{0.2}Na_{0.3}$ | 320 | 1000 | 5500 | 13.8 | 20 | 22.3 | 46.0 | 9.2 | 7.1 | 5.3 |
| 28 | $Li_{0.2}Na_{0.3}$ | 340 | 1300 | 3300 | 42.4 | 25.5 | 34.2 | 21.5 | 8.5 | 6.2 | 2.3 |
| 29 | $Mg_{0.2}Na_{0.3}$ | 320 | 1000 | 5500 | 15.3 | 27.3 | 34.2 | 21.5 | 8.5 | 6.2 | 2.3 |
| 30 | $Mg_{0.2}Na_{0.3}$ | 330 | 1300 | 3300 | 77.0 | 38.0 | 31.6 | 16.0 | 8.5 | 1.2 | 1.7 |
| 31 | $Na_{0.2}$ | 350 | 1300 | 3300 | 35.5 | 29.4 | 29.2 | 25.0 | 11.2 | 3.0 | 2.3 |
| 32 | $Na_{0.5}$ | 340 | 1300 | 3300 | 46.1 | 24.5 | 30.6 | 27.0 | 11.7 | 4.0 | 2.3 |
| 33 | $Cs_{0.2}$ | 350 | 1300 | 3300 | 17.0 | 72.8 | 8.1 | 12.4 | 6.7 | — | — |
| 34 | $Li_{0.4}$ | 320 | 1000 | 5500 | 13.2 | 27.5 | 29.4 | 25.6 | 12.9 | 2.6 | 2.0 |
| 35 | $Li_{0.4}$ | 330 | 1300 | 3300 | 43.5 | 34.4 | 35.1 | 15.8 | 10.6 | 2.1 | 2.0 |

We claim:

1. A process for the upgrading of synthesis gas to obtain selectivity to olefins and carboxylic acids comprising contacting carbon monoxide and hydrogen in the vapor phase at a reaction temperature of at least 250° C. and a reaction pressure of at least 500 psi with a catalyst of the formula $$M_aA_bRuCu_cN_zO_x$$

wherein
A is an alkali metal or an alkaline earth metal or mixtures thereof,
wherein
M is Ce, Cr, Fe, Mn, Mo, Zn or mixtures thereof, and
wherein
a is 0 to about 0.5
b is about 0.002 to about 2,
c is about 0.5 to about 3,
z is 0 to about 1 weight percent and
x is the number of oxygens needed to fulfill the valence requirements of the other elements.

2. A process as in claim 1 wherein A is selected from Na, Li, K, Rb, Cs, Mg or mixtures thereof.
3. A process as in claim 1 wherein a is 0.1 to 0.5.
4. A process as in claim 1 wherein b is 0.02 to 1.
5. A process as in claim 1 wherein c is about 1.
6. A process as in claim 1 wherein said catalyst is partially reduced.
7. A process as in claim 1 wherein said catalyst is supported on an inert carrier.
8. A process as in claim 7 wherein said carrier is selected from alumina, silica, alumina-silica, Alundum, clay, and silicon carbide.
9. A process as in claim 1 wherein the ratio of carbon monoxide to hydrogen is 10:1 to 1:10.
10. A process as in claim 1 wherein the ratio of carbon monoxide to hydrogen is 3:1 to 1:3.
11. A process as in claim 1 wherein the reaction temperature is about 275° to about 375° C.
12. A process for the upgrading of synthesis gas to yield hydrocarbons, alcohols and esters useful for fuel, comprising contacting carbon monoxide and hydrogen in the vapor phase at a temperature of at least 250° C. and a pressure of at least 500 psi in the presence of the catalyst of the formula $M_a A_b RuCu_c N_z O_x$ wherein
A is an alkali metal or an alkaline earth metal or a mixture thereof,
wherein
M is Ce, Cr, Fe, Mn, Mo, Zn or mixtures thereof, and
wherein
a is 0 to about 0.5,
b is about 0.002 to about 2,
c is about 0.5 to about 3,
z is 0 to about 1 weight percent and
x is the number of oxygens needed to fulfill the valence requirements of the other elements;
recovering the resulting hydrocarbon and oxygenated hydrocarbon products;
contacting said products with hydrogen at elevated temperature and pressure in the presence of a hydrogenation catalyst.

13. A process as in claim 12 wherein said products are contacted with hydrogen at a temperature of at least 200° C.
14. A process as in claim 12 wherein said products are contacted with hydrogen at a pressure of about 500 psi to 5,000 psi.
15. A process as in claim 12 wherein said hydrogenation catalyst is represented by the formula $G_e Ru_f D_g E_h O_x$ wherein
G=Zn, Cd and mixtures thereof;
D=Co, Ni and mixtures thereof;
E=Fe, Cu, Rh, Pd, Os, Ir, Pt and mixtures thereof;
and wherein
e=0 to 1,
f=0.01 to 3,
g=0.01 to 3,
h=0 to 1,
x=the number of oxygens determined by the valence requirements of the other elements.

16. A process as in claim 15 wherein said hydrogenation catalyst has the formula $RuCoPdZn_{0.4}O_x$.

17. A process for producing a hydrocarbon mixture comprising predominantly olefins and carboxylic acids, said process comprising contacting a gaseous reactant containing carbon monoxide and hydrogen with a catalyst of the formula $A_b RuCu_c N_z O_x$ wherein
A is an alkali metal or an alkaline earth metal or mixture thereof, and
wherein
b is about 0.002 to about 2,
c is about 0.5 to about 3,
z is 0 to about 1 weight percent and
x is the number of oxygens needed to fill the valence requirements of the other elements.

18. A process as in claim 17 wherein A is selected from the group consisting of Na, Li, K, Rb, Cs, Mg or a mixture thereof.
19. A process as in claim 17 wherein b is about 0.02 to about 1.
20. A process as in claim 17 wherein c is about 1.
21. A process as in claim 17 wherein said catalyst is partially reduced.
22. A process as in claim 17 wherein said catalyst is supported on an inert carrier.
23. A process as in claim 22 wherein said carrier is selected from alumina, silica, alumina-silica, Alundum, clay, and silicon carbide.
24. A process as in claim 17 wherein the ratio of carbon monoxide to hydrogen is about 10:1 to about 1:10.
25. A process as in claim 17 wherein the ratio of carbon monoxide to hydrogen is about 3:1 to about 1:3.
26. A process as in claim 17 wherein the reaction temperature is at least about 250° C. and the reaction pressure is at least about 500 psi.
27. A process as in claim 17 wherein the reaction temperature is about 275° C. to about 375° C.
28. A process as in claim 17 wherein said gaseous reactant is synthesis gas.
29. A process for producing a mixture of alkanes, esters and alcohols suitable for admixture with a fuel comprising
contacting a gaseous reactant containing carbon monoxide and hydrogen with a ruthenium-copper complex catalyst of the formula $A_b RuCu_c N_z O_x$ wherein
A is an alkali metal or an alkaline earth metal or a mixture thereof, and
wherein b is about 0.002 to about 2,
c is about 0.5 to about 3,
z is 0 to about 1 weight percent and
x is the number of oxygens needed to fill the valence requirements of the other elements:
recovering the resulting product:
contacting said product with hydrogen at elevated temperature and pressure in the presence of a hydrogenation catalyst.

30. A process as in claim 29 wherein said product is contacted with hydrogen at a temperature of at least 200° C.

31. A process as in claim 29 wherein said product is contacted with hydrogen at a pressure of about 250 psig to about 5000 psig.

32. A process as in claim 29 wherein said hydrogenation catalyst is represented by the formula $$G_e Ru_f D_g E_h O_x$$

wherein
G is Zn, Cd or a mixture thereof:
D is Co, Ni or a mixture thereof:
E is Fe, Cu, Rh, Pd, Os, Ir, Pt or a mixture thereof: and wherein
e is 0 to about 1,
f is about 0.01 to about 3,
g is about 0.01 to about 3,
h is 0 to about 1, and
x is the number of oxygens needed to fill the valence requirements of the other elements.

33. A process as in claim 32 wherein said hydrogenation catalyst has the formula $RuCoPdZn_{0.4}O_x$.

34. A process as in claim 29 wherein A is selected from the group consisting of Na, Li, K, Rb, Cs, Mg or a mixture thereof.

35. A process as in claim 29 wherein b is about 0.02 to about 1.

36. A process as in claim 29 wherein c is about 1.

37. A process as in claim 29 wherein said ruthenium-copper complex catalyst is partially reduced.

38. A process as in claim 29 wherein said ruthenium-copper complex catalyst is supported on an inert carrier.

39. A process as in claim 38 wherein said carrier is selected from alumina, silica, alumina-silica, Alundum, clay, and silicon carbide.

40. A process as in claim 29 wherein the ratio of carbon monoxide to hydrogen is about 10:1 to about 1:10.

41. A process as in claim 29 wherein the ratio of carbon monoxide to hydrogen is about 3:1 to about 1:3.

42. A process as in claim 29 wherein said gaseous reactant is synthesis gas.

43. A process as in claim 29 wherein said gaseous reactant is contacted with said ruthenium-copper complex catalyst at a temperature of at least about 250° C. and a pressure of at least about 500 psi.

44. A process as in claim 29 wherein said gaseous reactant is contacted with said ruthenium-copper complex catalyst at a temperature in the range of about 275° C. to about 375° C.

* * * * *